United States Patent
Bigio et al.

(10) Patent No.: US 6,381,018 B1
(45) Date of Patent: *Apr. 30, 2002

(54) METHOD FOR MEASURING CHANGES IN LIGHT ABSORPTION OF HIGHLY SCATTERING MEDIA

(75) Inventors: Irving J. Bigio; Tamara M. Johnson; Judith R. Mourant, all of Los Alamos, NM (US)

(73) Assignee: The Regents of the University of California, Los Alamos, NM (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/363,270

(22) Filed: Jul. 27, 1999

Related U.S. Application Data (60) Provisional application No. 60/094,460, filed on Jul. 28, 1998.

(51) Int. Cl.[7] ............................................... G01N 21/00
(52) U.S. Cl. ..................... 356/432; 356/326; 600/476; 600/478
(58) Field of Search .................. 356/73, 432–435, 356/338–343, 445, 39, 446, 40, 318, 326; 385/12, 115, 116, 117; 600/310, 316, 476, 478; 7/317–329, 337, 342, 339.12; 250/227.27

(56) References Cited

U.S. PATENT DOCUMENTS

| | | | | |
|---|---|---|---|---|
| 5,303,026 A | * | 4/1994 | Strobl et al. | 356/318 |
| 5,522,868 A | * | 6/1996 | Buckley et al. | 607/94 |
| 5,555,885 A | * | 9/1996 | Chance | 128/654 |
| 5,676,142 A | * | 10/1997 | Miwa et al. | 128/633 |
| 5,822,072 A | * | 10/1998 | Dai et al. | 356/436 |
| 6,014,204 A | * | 1/2000 | Prahl et al. | 356/73 |
| 6,015,969 A | * | 1/2000 | Nathel et al. | 250/227.27 |

OTHER PUBLICATIONS

Mourant et al, Measuring Absorption Coefficients In Small Volumes Of Highly Scattering Media: Source–Detector Separations For Which Pathlengths Do Not Depend On Scattering Properties, Applied Optics 36, No. 22 5655, Aug. 1, 1997.*

"Measuring Absorption Coefficients in Small Volumes of Highly Scattering Media: Source–Detector Separations for Which Pathlengths Do Not Depend on Scattering Properties," printed in Applied Optics 36, No. 22, 5655 (Aug. 1, 1997).

G. Kumar and J.M. Schmitt, "Optimal Probe Geometry For Near–Infrared Spectroscopy Of Biological Tissue," Applied Optics 36, 2286 (1997).

Judith R. Mourant, Tamara M. Johnson, Gerrit Los, and Irving J. Bigio, "Non–invasive Measurement Of Chemotherapy Drug Concentrations In Tissue: Preliminary Demonstrations Of In Vivo Measurements," Phys. Med. Biol. 44, 1397 (1999).

* cited by examiner

*Primary Examiner*—Hoa Q. Pham
(74) *Attorney, Agent, or Firm*—Samuel M. Freund (57) ABSTRACT

The noninvasive measurement of variations in absorption that are due to changes in concentrations of biochemically relevant compounds in tissue is important in many clinical settings. One problem with such measurements is that the pathlength traveled by the collected light through the tissue depends on the scattering properties of the tissue. It is demonstrated, using both Monte Carlo simulations and experimental measurements, that for an appropriate separation between light-delivery and light-collection fibers, the pathlength of the collected photons is insensitive to scattering parameters for the range of parameters typically found in tissue. This is important for developing rapid, noninvasive, inexpensive, and accurate methods for measuring absorption changes in tissue.

8 Claims, 11 Drawing Sheets

METHOD FOR MEASURING CHANGES IN LIGHT ABSORPTION OF HIGHLY SCATTERING MEDIA

CROSS-REFERENCE TO RELATED APPLICATIONS

The present Nonprovisional Patent Application claims the benefit of copending Provisional Application No. 60/094,460, filed on Jul. 28, 1998.

This invention was made with government support under Contract No. W-7405-ENG-36 awarded by the U.S. Department of Energy. The government has certain rights in the invention.

FIELD OF THE INVENTION

The present invention relates generally to the noninvasive measurement of optically absorbing compounds in turbid media including concentrations of biochemically relevant compounds in tissue and, more particularly, to a method for noninvasively measuring absorption changes in tissue where the pathlength in the tissue of the collected photons is insensitive to changes in the scattering parameters of the tissue.

BACKGROUND OF THE INVENTION

Noninvasive in vivo methods for measuring absorption coefficients of tissue are potentially useful biomedical tools. Applications include measurements of endogenous compounds such as hemoglobin, bilirubin, and cytochrome oxidase, as well as determining concentrations of exogenous chromophores such as photodynamic therapy and chemotherapy drugs. The specific case of chemotherapy drugs can be used to illustrate the potential benefits of a noninvasive or minimally invasive method for measuring local tissue concentrations. The therapeutic benefit of chemotherapy drugs is determined by the tissue concentration of the drug in the targeted site. The only minimally invasive measurement available to the oncologist is to track the blood-serum concentration and assume a particular relationship to the tissue concentration, which is generally unreliable. Spectroscopic investigation of tissue for concentrations of species is generally performed in reflectance. However, baseline variations in unprocessed spectra generally overwhelm the absorption spectral features. Reflectance values measured on different sites on the same person, or from the same site on different people, can differ substantially even when the absorber is present in the same concentration. The scattering coefficient of biological tissue depends on the concentration of interstitial water, the density of structural fibers, and the shapes and sizes of cellular structures, to name just three factors. Other methods for tracking pharmicokinetics locally, such as microdialysis, are invasive. Moreover, microdialysis measures only the intercellular fluid and provides no information about drug concentrations inside the cells, a key issue for chemotherapy agents. The ability to noninvasively track compound concentrations by examining changes in absorption that are due to the presence of the drug in the target tissue would be useful in clinical pharmacology, especially for the development of new drugs.

Most work to date has concentrated on making optical measurements, in a geometry for which the diffusion approximation is applicable, although neural-network and Monte Carlo analyses have been used to examine situations where the diffusion approximation does not hold. In "Optimal Probe Geometry For Near-Infrared Spectroscopy Of Biological Tissue," by G. Kumar and J. M. Schmitt, Applied Optics 36, 2286 (1997), the authors discuss the influence of probe geometry on spectroscopic absorption measurements obtained from the surface of turbid biological tissue. Basically, a source of light and a detector for backward scattered light are placed in close proximity to each other on the surface of the tissue to be investigated. In particular, although the choice of probe design is commonly dictated by commercial availability rather than by optimization, it was found that a range of probe spacings exists in which scattering variations have the least effect on fluence measurements. In addition, by choosing the separation between the source and detector probes (for small-diameter fibers) to be between 2 and 5 mm, Kumar and Schmitt have minimized the sensitivity of the detected fluence to the ratio of the fractional sensitivities, to the reduced scattering coefficients, $\mu_s'$, and to the absorption coefficient, $\mu_a$, for anisotropically scattering biological tissue with scattering coefficients in the range between 0.5 and 1.5 $mm^{-1}$. Kumar and Schmitt suggest that this also improves the accuracy of absorption measurements made on such tissues. Kumar and Schmitt, however, do not teach either theoretically or experimentally that maximizing the ratio of the fractional sensitivities to $\mu_s'$ and $\mu_a$ optimizes the accuracy of measurements of $\mu_a$.

Accordingly, it is an object of the present invention to provide an apparatus for spectroscopically measuring absorption of target species in turbid media where the pathlength traveled by the collected light through the medium is minimally dependent on the scattering parameters of the medium, such that small changes in absorption can be measured independent of variations in scattering.

Additional objects, advantages and novel features of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus for measuring absorption of light by a material in a small volume of highly scattering medium of this invention may include: a source of light having a wavelength which is absorbed by the material; a first optical fiber for receiving the light and directing it onto the surface of the medium, such that the light enters the medium; a second optical fiber located a chosen distance from the first optical fiber on the surface of the highly scattering media for collecting and receiving a portion of the light scattered from the medium in a direction opposite to the direction of the light entering the medium; and a light detector for detecting light exiting the second optical fiber, whereby the distance between the first optical fiber and the second optical fiber is chosen such that the dependence of the pathlength of the light entering the medium taken to reach the second fiber on the scattering parameters of said highly scattering medium is minimized, and a measurement of the light absorbed by a portion of the material is obtained.

Preferably, the chosen distance between the first optical fiber and the second optical fiber on the surface of the medium is about 1.7 mm.

It is also preferred that the diameter of the first optical fiber and the diameter of the second optical fiber are less than 400 $\mu$m.

Preferably also, the second end of the first optical fiber and the first end of said second optical fiber are placed in direct optical contact with the highly scattering material in order that surface reflections are minimized and that all of the collected light has undergone multiple scattering through the highly scattering material.

BRIEF DESCRIPTION OF THE DRAWINGS

The accompanying drawings, which are incorporated in and form a part of the specification, illustrate one embodiment of the present invention and, together with the description, serve to explain the principles of the invention. In the drawings:

FIG. 2a is a schematic representation of the apparatus used to demonstrate the method of the present invention, while

FIG. 4(a) is a graph of the areas under absorption curves from 575 to 595 nm of analyzed spectra as a function of the average absorption coefficient of the blue dye from 575 to 595 nm; dye was added to the scattering solutions for a source-detector separation of 1.42 mm, while

DETAILED DESCRIPTION

Briefly, the present invention includes a method for measuring small absorption changes in turbid media, for which the diffusion approximation is not valid, by detecting light which has been backscattered by the medium. Rather than frequency domain or time-resolved measurements, steady-state measurements are undertaken, which permits a wavelength range greater than 500 nm to be measured in less than 1 s. As will be explained in detail hereinbelow, when light is both introduced into a material and collected using fiber optics in contact with the surface of the material, there is an optimum separation between the source and the detector fibers for which the dependence of the pathlength on scattering parameters is minimized. This is essential for insuring that absorption measurements are meaningful, and can be understood by examining optical pathlengths for turbid absorbers for the limiting cases of small and large source-detector separations. In general, for small fiber separations, the average pathlength of collected photons is longer for a less-scattering medium (higher g values) than for a highly scattering medium (lower g values, where g=<cos θ>) because the photons must undergo a certain number of high-angle scattering events to essentially reverse their direction of travel. At large fiber separations, by contrast, the pathlength is expected to be longer for more highly scattering media, as is the situation for light transmitted through a turbid medium. Therefore, there must be a region for which the average pathlengths for different scattering media are similar.

Knowledge of the pathlength L traveled by collected photons permits the use of Beer's law, given in Equation 1, where I is the collected light, $\mu_s$ is the absorption coefficient of the medium, and $I_0$ is the incident light intensity:

$$I = I_o \exp(-\mu_a L). \tag{1}$$

It is assumed that the pathlength does not depend on wavelength. By comparing the signals at two different wavelengths, it is possible to determine the difference in absorption coefficients at the two wavelengths as:

$$\mu_a(\lambda_1) - \mu_a(\lambda_2) = -\ln\left[\frac{I(\lambda_1)/I_o(\lambda_1)}{I(\lambda_2)/I_o(\lambda_2)}\right]/L. \tag{2}$$

For a chromophore with a sharp absorption band (that is, there is absorption at $\lambda_1$, but not $\lambda_2$), Equation 2 has utility for measuring changes in the concentration of a chromophore when L is known. As will be shown hereinbelow, for certain source-detector separations, the pathlength depends only weakly on the scattering properties over the range found in tissue. Small changes in absorption are also found to have a negligible effect on pathlength. Therefore, if the difference in absorption at $\lambda_1$ and $\lambda_2$ is small (which is what is of interest for the present invention) and appropriate fiber separations are chosen, the above assumption that the pathlength does not depend on wavelength is valid.

To investigate characteristics of light scattering with small source-detector separations, Monte Carlo simulations were performed using known procedures. Reflection and refraction at interfaces between different media and the numerical aperture of the light-delivery and light-collection fibers are accounted for in the code. Henyey-Greenstein phase functions were used in the simulation, and the effects of different values of g=<cos θ>), the average value of the cosine of the angle, θ, through which the light is scattered, were assessed. The delivery and collection fibers were modeled as being 200 μm in diameter with a numerical aperture of 0.34.

Figure 1:
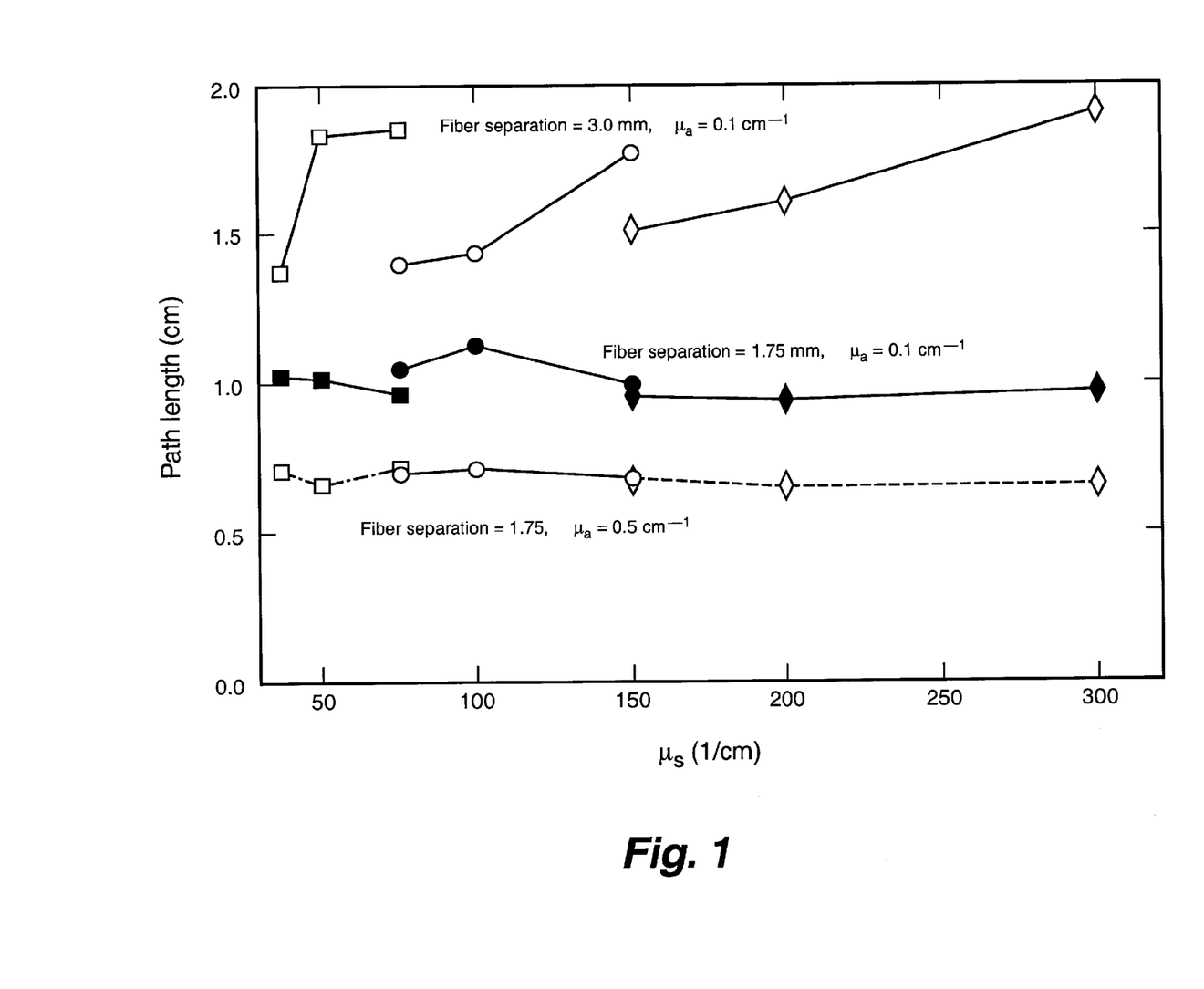
FIG. 1 is a graph of the average pathlengths of photons traveling from a delivery fiber to a collection fiber (in a backscatter geometry such as that shown in FIG. 2, hereof), as a function of the scattering parameter of the medium, calculated by Monte Carlo simulations.

Reference will now be made in detail to the present preferred embodiments of the invention, examples of which are illustrated in the accompanying drawings. Identical callouts are used to represent similar or identical structure therein. Turning now to the FIGURES, FIG. 1 is a graph of the average path traveled by the collected photons plotted as a function of the scattering coefficient, $\mu_s$, of the medium with the anisotropy factor, g, adjusted to keep $\mu_s'=\mu_s(1-g)$ within the range 7.5–15 cm$^{-1}$. Results are shown for three sets of source- and detector-fiber center-to-center separations, d, and values of $\mu_a$. For d=1.75 and $\mu_a$=0.5 cm$^{-1}$ the greatest percent variation in pathlength for different scattering parameters is 9.5%. For d=1.75 and $\mu_a$ 32 0.1 cm$^{-1}$, the difference in pathlengths is ~16%, while for d=3.0 and $\mu_a$=0.1 cm$^{-1}$, the percent difference in pathlengths is 30%. The error bars are smaller than the symbols and were determined by several simulations with different numbers of incident photons. Simulations in which more than 400 photons were collected resulted in the same value (to within 0.1%) of the pathlength. Deviations from this value when smaller numbers of photons were collected were used to estimate the errors.

This demonstrates that for the correct choice of fiber separation the average pathlength traveled by the collected photons depends only weakly on scattering characteristics. Issues regarding FIG. 1 are: (1) whether the substantial lack of dependence on scattering properties is valid for the range of absorption parameters found in tissue, and (2) whether the choice of fiber separation and the variation in pathlength depend on properties of the optical delivery and collection systems. Concerning the latter issue, fiber numerical aperture was found to have a negligible effect on the pathlength. Pathlengths determined from Monte Carlo simulations with numerical apertures of 0.22 and 0.34 agreed within the error limits for all but two data points for d=1.75 and $\mu_a$=0.5 cm$^{-1}$.

The average pathlengths of photons traveling from a source to a collection fiber may not be the same in media having the same light scattering properties, but different absorption coefficients. To investigate how this might affect the choice of optimal fiber separation, simulations with the same scattering parameters as in FIG. 1 were performed, but with absorption coefficients of 2.0 cm$^{-1}$ and 0.1 cm$^{-1}$. For an absorption coefficient of 2 cm$^{-1}$, it was found that at source-detector separations of 1.25, 1.75, and 2.25 mm, the variation in pathlengths was 17%, 7%, and 14%, respectively. For an absorption coefficient of 0.1 cm$^{-1}$ there is a 40% variation between the longest and the shortest average pathlengths at a separation of 1.0 mm. At fiber separations of 1.5, 1.75 (see FIG. 1), 1.87, and 2.0 mm the variation in pathlengths is 16%–20%. When fiber separation is increased to 3.0 mm, the variation in pathlengths again increases to ~40% (see FIG. 1). This suggests that there is a range of fiber separations for which the pathlength is nearly independent of scattering parameters. Furthermore, the choice of optimum source-detector separation may be valid for a range of absorption coefficients. For example, the 1.75-mm separation is found to have less than a 10% variation in pathlength as a function of scattering properties when the absorption coefficient is 0.5 cm$^{-1}$ would also work well for measurements in a medium with an absorption coefficient of 0.1 or 2.0 cm$^{-1}$.

Figure 2A:
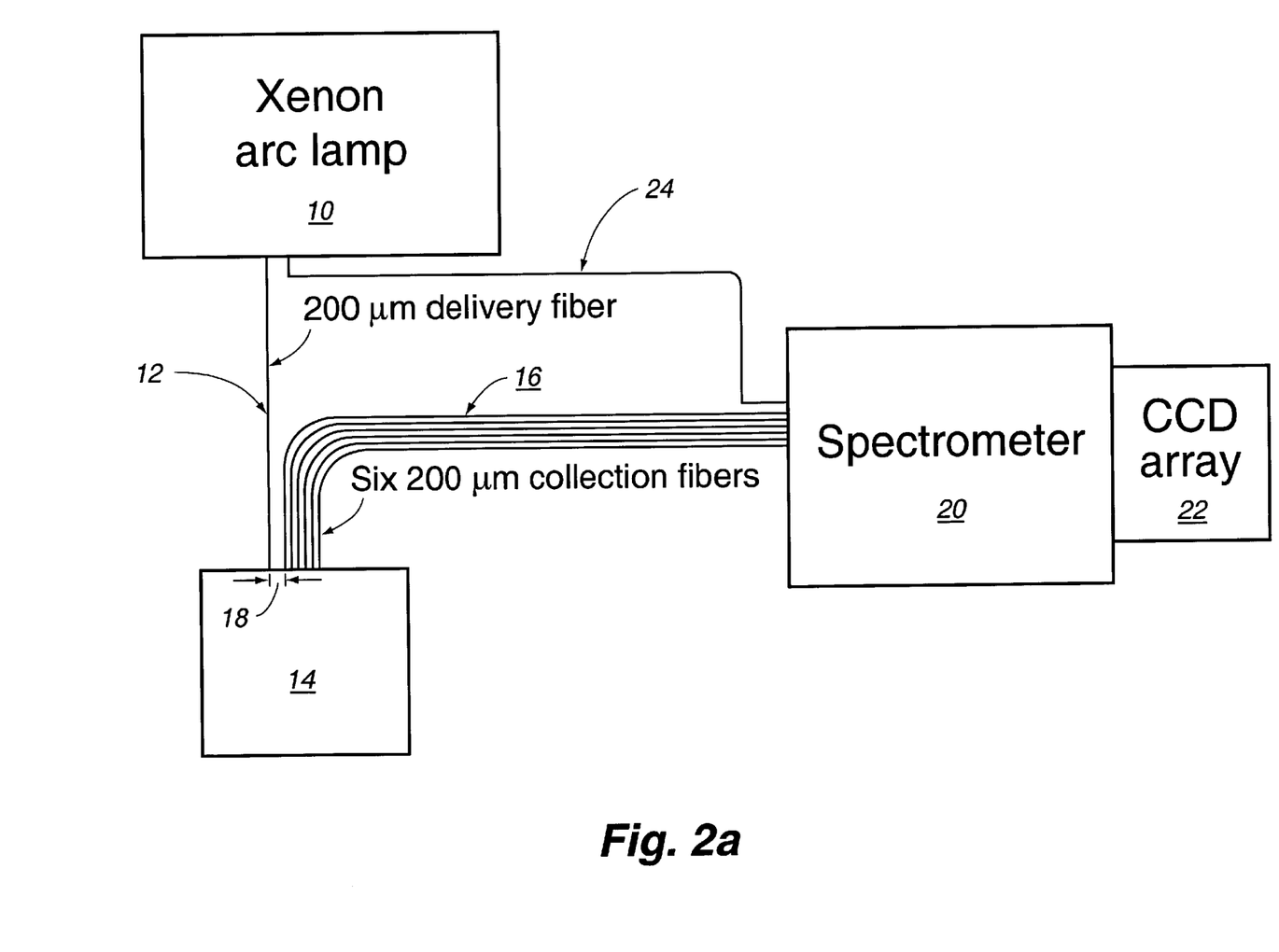

FIG. 2a is a schematic representation of the apparatus used to demonstrate the method of the present invention. The output from cw xenon arc lamp, 10, was directed into one end of delivery optical fiber, 12, which was 200 μm in diameter and had a numerical aperture of 0.22. The other end of fiber 12 was placed in the vicinity of the surface of tissue phantom, 14. Several fibers, 16, also 200 μm in diameter and having a numerical aperture of 0.22, were used for light collection in the vicinity of the surface of the surface of the tissue phantom at different distances from the delivery fiber 12. The incident light power on the sample was ~1.5 mW. The delivery-collector fiber separations, d, 18, were 0.7, 0.95, 1.2, 1.42, 1.7, 2.18, 2.4, 2.65, 2.98, and 3.2 mm. Light from eight of the collection fibers was simultaneously dispersed by spectrograph, 20, and focused onto a two-dimensional thermoelectrically cooled CCD array, 22. In this manner one axis of the CCD array corresponded to wavelength, while the other axis corresponded to collection fibers at different distances from the source fiber. Signal integration times were ≦1 s. To account for any fluctuations in lamp intensity, a portion of the light from the lamp 10 was attenuated and directed to spectrometer 20 through fiber, 24.

Figure 2B:
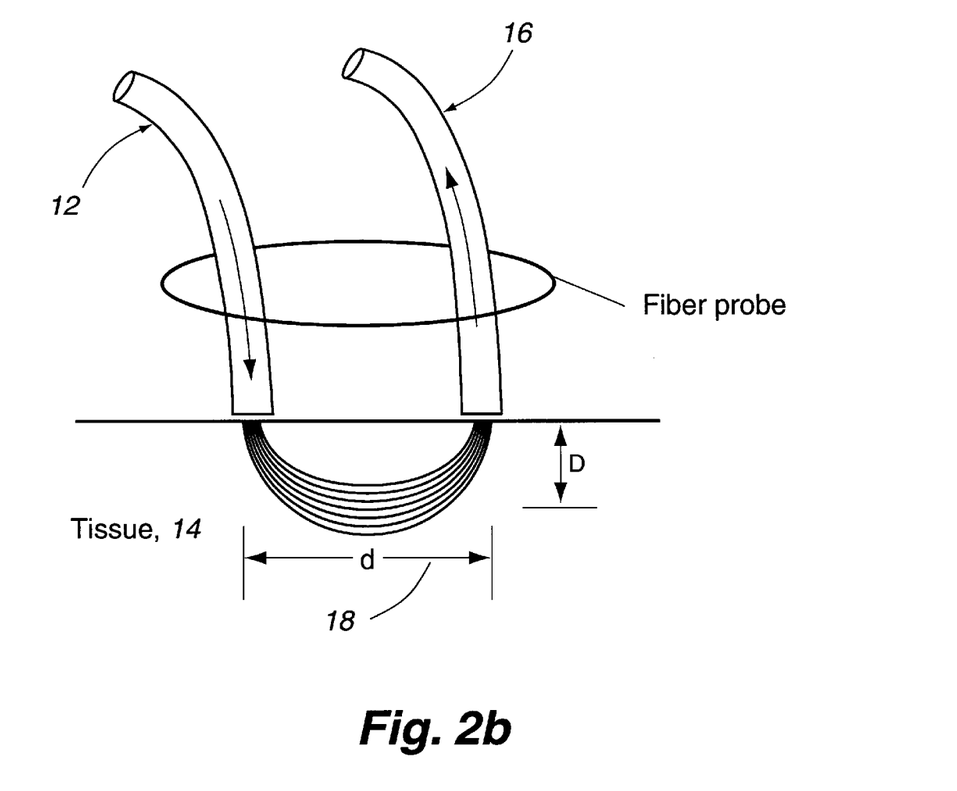
FIG. 2b is an expanded schematic representation of the region of interaction between the illuminating and light collecting fibers and the tissue under investigation.
Figure 2C:
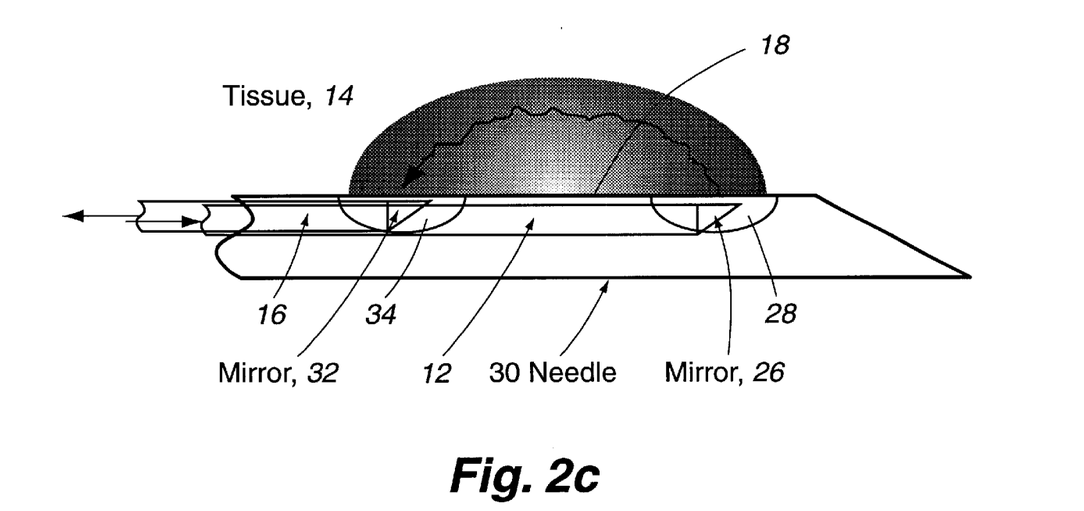
FIG. 2c is a schematic representation of a more compact probe design where the illuminating and light collecting fibers are disposed longitudinally along the length of a needle-shaped probe.

FIG. 2b is an expanded schematic representation of the region of interaction between the fiber probe and the tissue under investigation. The separate illuminating, 12, and collecting, 16, fibers are placed in direct optical contact with the tissue in order to avoid surface reflections and to insure that all of the collected light has undergone multiple scattering through the tissue in passing between the illuminating fiber and the collecting fiber. The spacing between the illuminating and collecting fibers 18 is also denoted by "d", while the average penetration distance of detected light is denoted by "D". FIG. 2c is a schematic representation of a more compact probe design is a schematic representation of a more compact probe design where the illuminating and light collecting fibers are disposed longitudinally along the length of a needle-shaped probe. Here light travelling through illuminating fiber 12 is directed onto turning mirror, 26, which reflects the light through hole, 28, in needle-shaped probe, 30. Turning mirror, 32, directs light exiting tissue 14 through hole, 34, in needle 30 into collecting fibers 16. Although the probe design illustrated in FIGS. 2a and 2b hereof exceeds the dimensions of many standard endoscopes when the illuminating and collecting fibers are spaced at the optimum distance, d, 18, the more compact probe design shown in FIG. 2c hereof will successfully address this problem.

Aqueous suspensions of polystyrene spheres and lntralipid-10% (Pharmacia, Inc., Clayton, N.J.) were used as scattering media. Measurements were made in 5%, 10%, and 15% concentrations of Intralipid-10%. These concentrations correspond to reduced scattering coefficients of 7, 15, and 22 cm$^{-1}$ at 550 nm, and reduced scattering coefficients of 5, 10, and 16 cm$^{-1}$ at 650 nm. The value of g at 550 nm is ~0.80, and at 650 nm it is ~0.79. Polystyrene spheres having diameters of either 0.890 or 0.913 μm, were used at concentrations of 0.2%, 0.4%, and 0.6% by weight. This corresponds to reduced scattering coefficients of ~7, ~14, and ~21 cm$^{-1}$ at 550 nm, where 9 =0.92, and reduced scattering coefficients of ~6, ~12, and ~18 cm$^{-1}$ at 650 nm, where g=0.91 as calculated by Mie theory. An index of refraction of 1.59 was used for the polystyrene spheres. Fifty milliliters of the suspensions were placed in standard 50-ml beakers and, as stated hereinabove, the optical fibers were placed on or near the surface of the suspensions for the measurements. For absorbers, India ink and the dye Direct Blue 71 (Aldrich Chemicals, Milwaukee, Wis., ACS number 4399-55-7) were used. The Direct Blue dye was added to the scattering solutions in aliquots so as to change the absorption coefficient by ~0.011 cm$^{-1}$ at 585 nm for each addition. Spectra were taken with no Direct Blue dye present and after each addition of Direct Blue dye.

Figure 3:
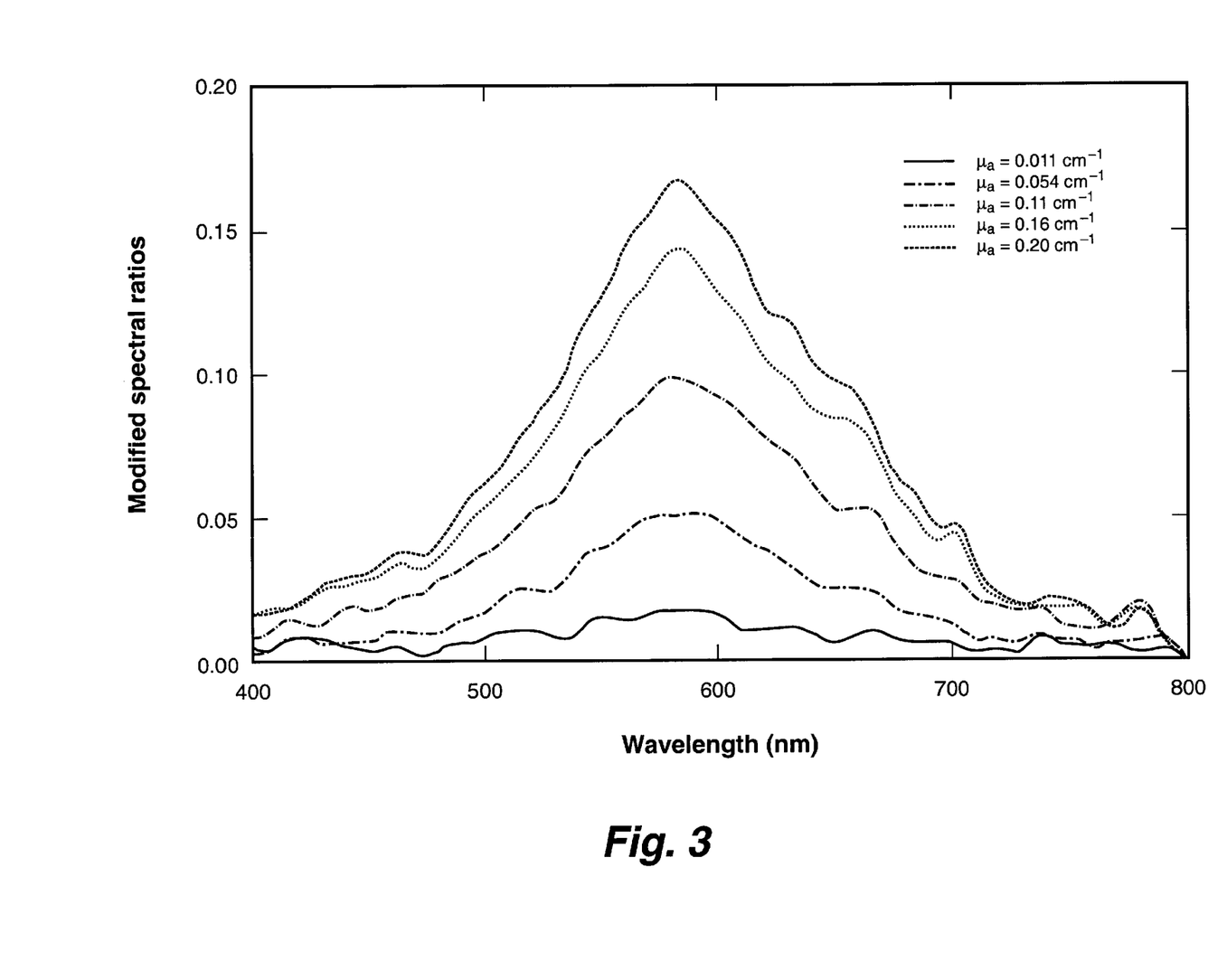
FIG. 3 shows spectra taken after the addition of Direct Blue dye, which have been divided by a spectrum of a sample having no Direct Blue dye, normalized at 800 nm (the ordinate representing the negative natural log of the ratios), and with a source/detector separation of 1.42 mm.

Data were analyzed by dividing each spectrum taken with Direct Blue dye present by the spectrum taken before Direct Blue dye was added. The spectra were then normalized to unity at 800 nm, a wavelength at which Direct Blue dye does not absorb. This normalization was performed because the level of the solution changed during the course of adding blue dye, which slightly changes the total amount of light detected, although it has no measurable effect on the wavelength dependence of collected light. Finally, the negative natural log was taken over the entire wavelength range. These spectra will be referred to as "analyzed spectra," examples of which are shown in FIG. 3. For FIG. 3, the scattering media was 10% Intralipid-10%, and the values of $\mu_a$ given in the box represent the average absorption coefficient of the scattering solution from 575 to 695 nm that is due to the addition of the Direct Blue dye. The source-detector separation of 1.42 mm.

Figure 4A:
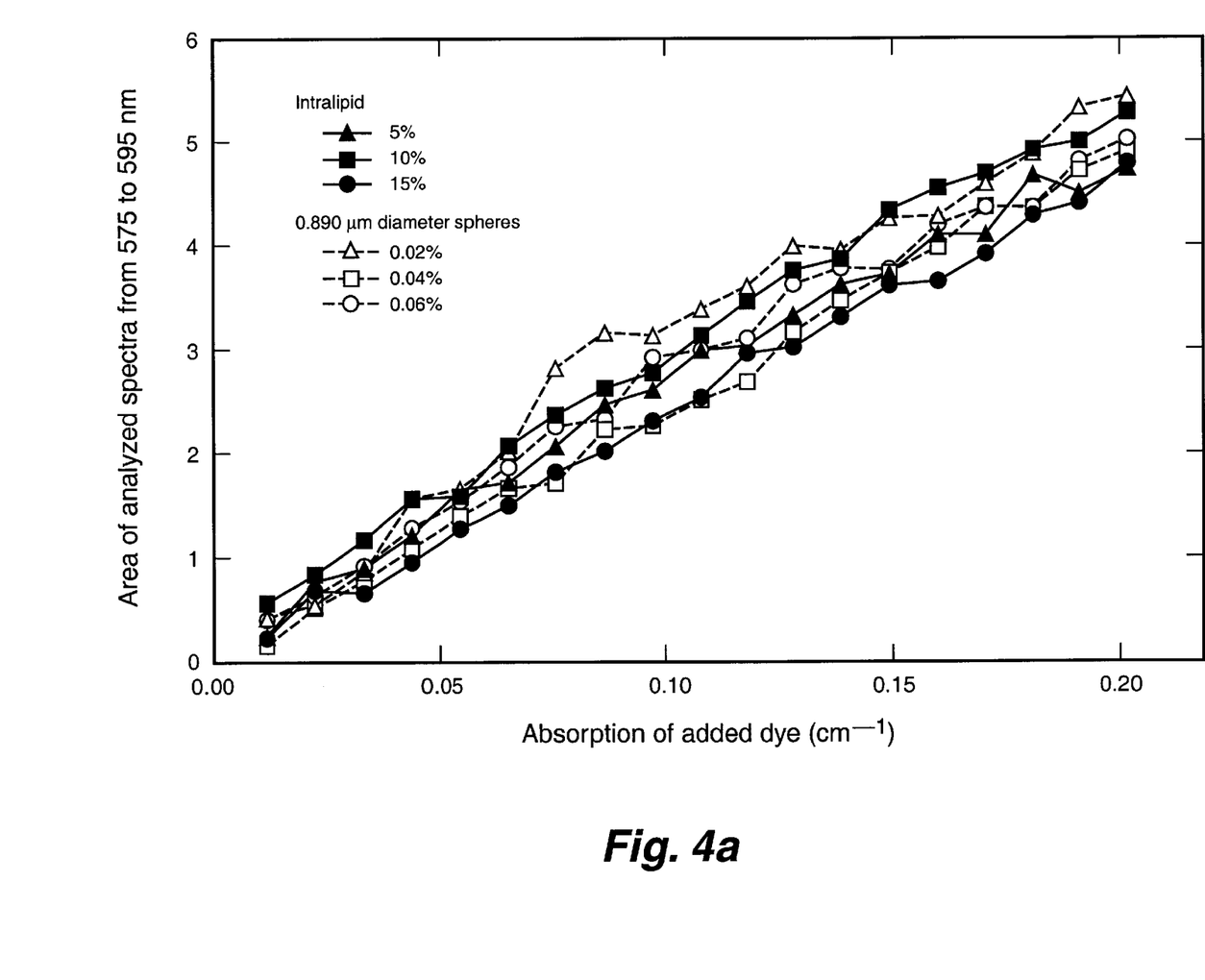
Figure 4B:
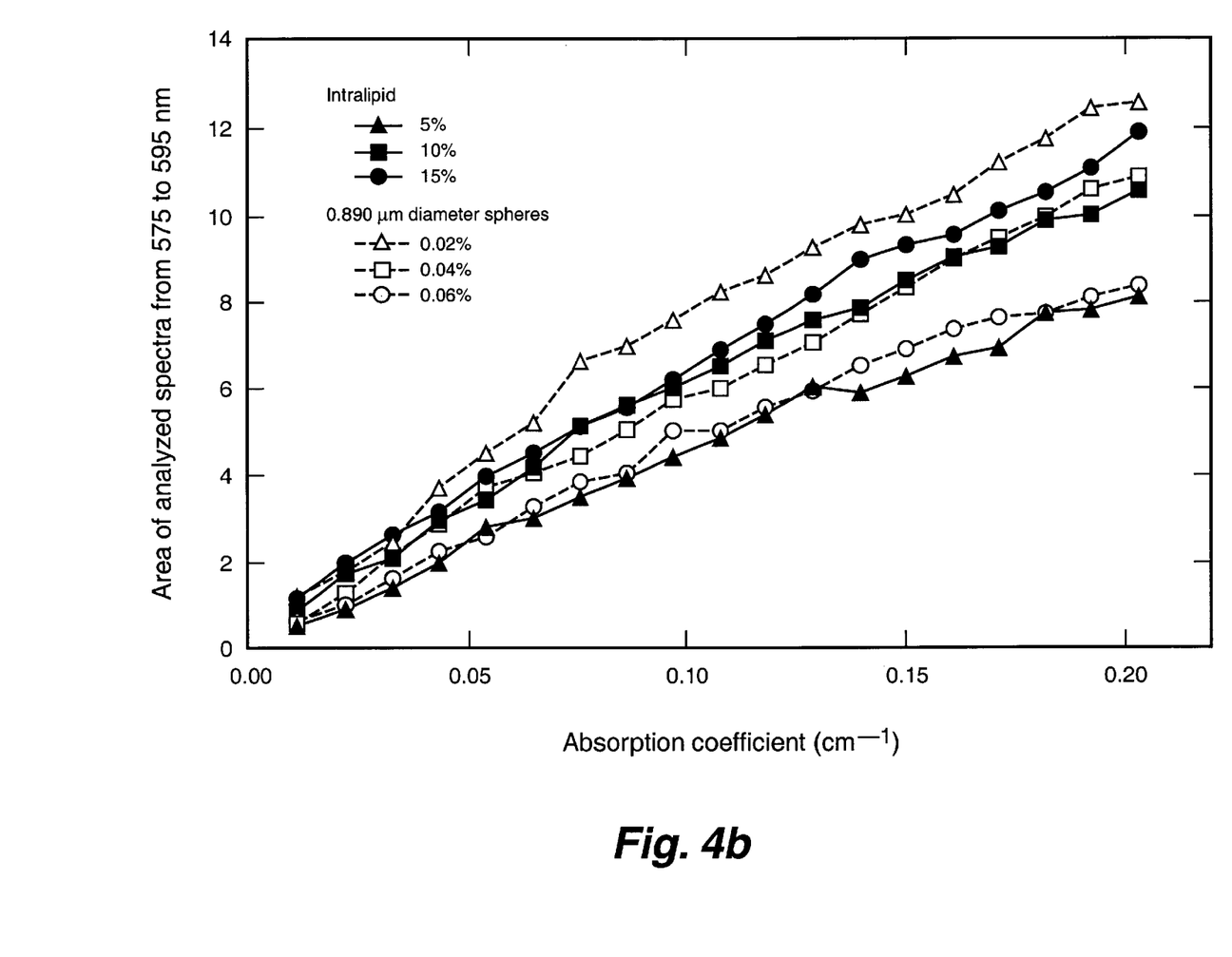
FIG. 4(b) shows the same areas for a fiber separation of 2.98 mm.

FIG. 4(a) is a plot of the area under the curves from 575 to 595 nm (approximately the peak of the absorption) shown in FIG. 3 as a function of the average absorption coefficient of the added blue dye at 585 nm. Dye was added to the scattering solutions for a source-detector separation of 1.42 mm. FIG. 4(b) shows the same areas for a fiber separation of 2.98 mm.

Figure 5:
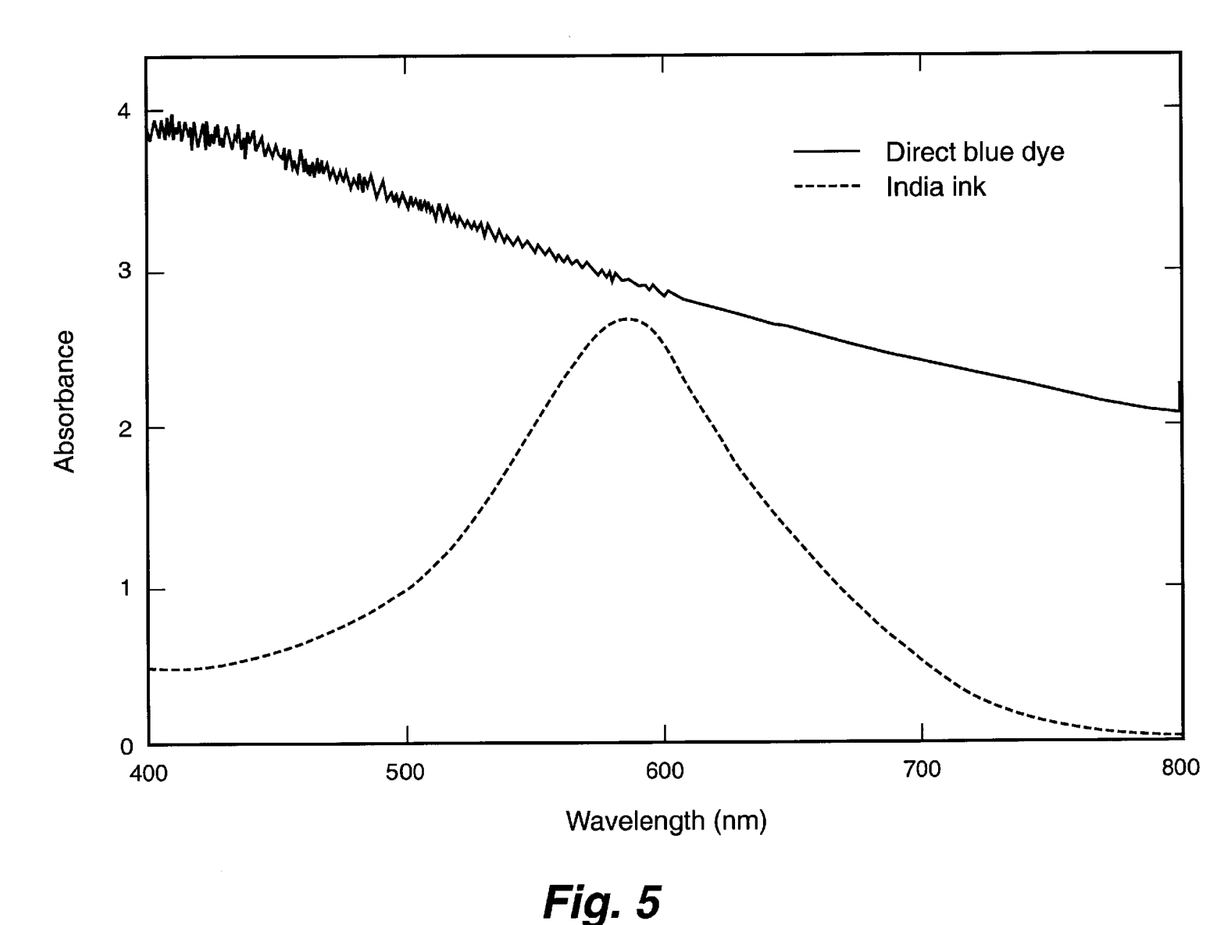
FIG. 5 shows the absorption spectra of India ink and blue dye as a function of wavelength.

The spectral shape of the Direct Blue dye in nonscattering, aqueous solutions of the Direct Blue dye was determined to be independent of dye concentration. Spectra of the blue dye and India ink are shown in FIG. 5.

Knowledge of the optimum fiber separation was employed for deducing the amount of Direct Blue dye added to a scattering solution. Measurements of scattering solutions of spheres with India ink were made before and after the addition of aliquots of Direct Blue dye. The data were analyzed without knowledge of the amount of dye that was added.

In FIG. 4(a) the areas under the traces of analyzed spectra (see FIG. 3) from 575 to 595 nm are plotted versus the absorption coefficient of the added blue dye at 585 nm for a source-fiber to detector-fiber separation of 1.42 mm. The different curves represent the six different scattering solutions. (India ink was not added to these scattering solutions.) Despite the large range of scattering properties in the different tissue phantoms, the curves in FIG. 4(a) are all similar. For both larger and smaller fiber separations the slopes of curves like those plotted in FIG. 4(a) depend strongly on scattering properties. This is shown for a fiber separation of 2.98 mm in FIG. 4(b).

Figure 6:
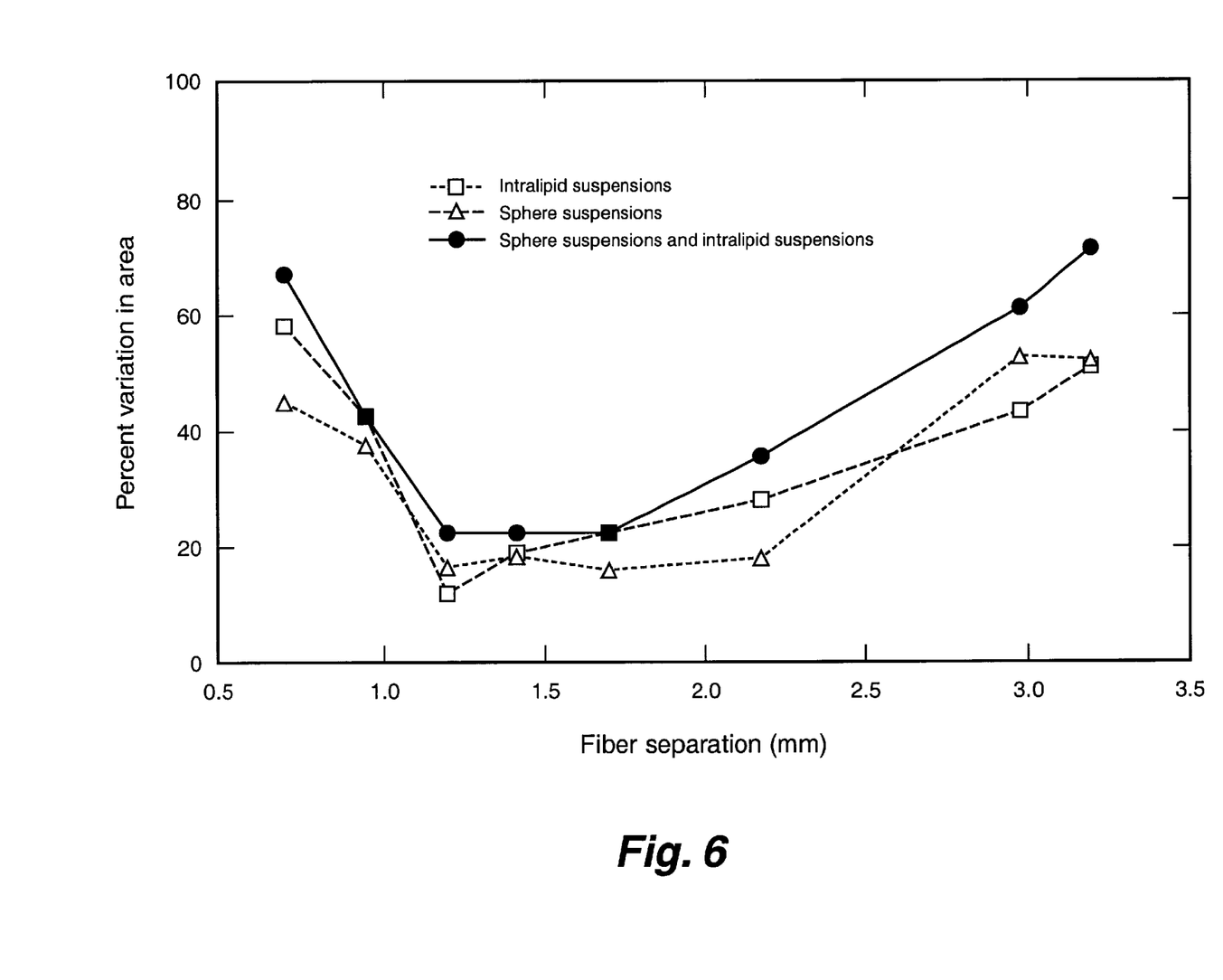
FIG. 6 shows the percent difference in the largest and smallest areas under the curve from 575 to 595 nm of the analyzed spectra as a function of the source-detector fiber separation. Analyzed spectra were used for which the amount of added Direct Blue dye had an absorption of 0.15 cm$^{-1}$ at 585 nm. The three scattering suspensions composed of 0.2%, 0.4%, and 0.6% 0.890-$\mu$m-diameter spheres had reduced scattering coefficients of ~6, ~12, and ~18 cm$^{-1}$ at 650 nm, where g=0.91. The three scattering suspensions composed of 5%, 10%, and 15% Intralipid-10% had reduced scattering coefficients of 5, 10, and 16 cm$^{-1}$ at 650 nm, where g=0.79.

To determine the best choice of fiber separation, the percent difference in the area from 575 to 595 nm of the analyzed spectra for the different scattering solutions was plotted versus the fiber separation in FIG. 6. This percent variation in area was calculated according to Eq. (3), where $A_{min}$ is the minimum value of the area from 575 to 585 nm and $A_{max}$ is the maximum value of the area from 575 to 595 nm for the set of scattering suspensions measured:

$$\text{percent variation} = \frac{A_{max} - A_{min}}{A_{min}} \times 100. \quad (3)$$

Values for $A_{min}$ and $A_{max}$ were determined by fitting the area curves (e.g., the curves in FIG. 4) to third-order polynomials and use of the values of the fits at an absorbance of 0.15 cm$^{-1}$. FIG. 6 shows the percent variation in the area from 575 to 595 nm of the analyzed spectra are shown for the Intralipid suspensions, for the sphere suspensions, and for the Intralipid and sphere suspensions combined. The percent variation in area is lowest at fiber separations from 1.2 to 2.2 mm.

Figure 7:
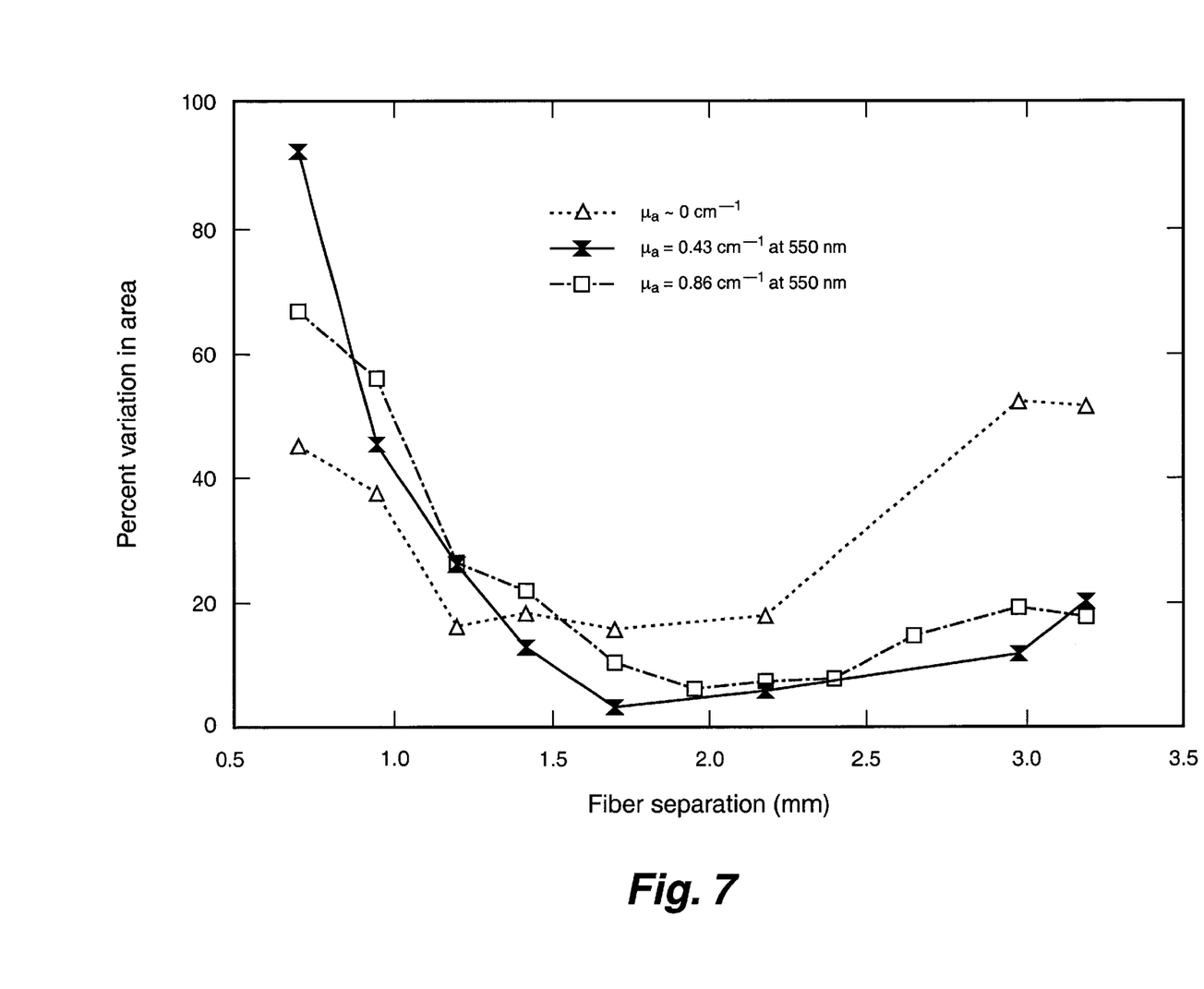
FIG. 7 shows the percent difference in the largest and the smallest areas under the curve from 575 to 595 nm of the analyzed spectra for the three scattering solutions composed of 0.2%, 0.4%, and 0.6% by weight 0.913 $\mu$m-diameter polystyrene spheres as a function of the source-detector fiber separation. Analyzed spectra were used for which the amount of added Direct Blue dye had an absorption of 0.15 cm$^{-1}$ at 585 nm. Data are given for three different values of $\mu_a$.

The effect of the absorption of the starting medium on the optimum choice of source-detector fiber separation was determined. The above measurements on the three different concentrations of polystyrene spheres were repeated, except that India ink was added to the original solutions to provide a background absorption. The percent difference in the areas from 575 to 595 nm of the analyzed spectra is plotted versus fiber separation in FIG. 7. The percent variation in area is smaller for the data with absorption coefficients of 0.4 and 0.8 cm$^{-1}$ than for the data taken with a background absorption of nearly zero for fiber separations greater than ~1.5 mm.

Figure 8:
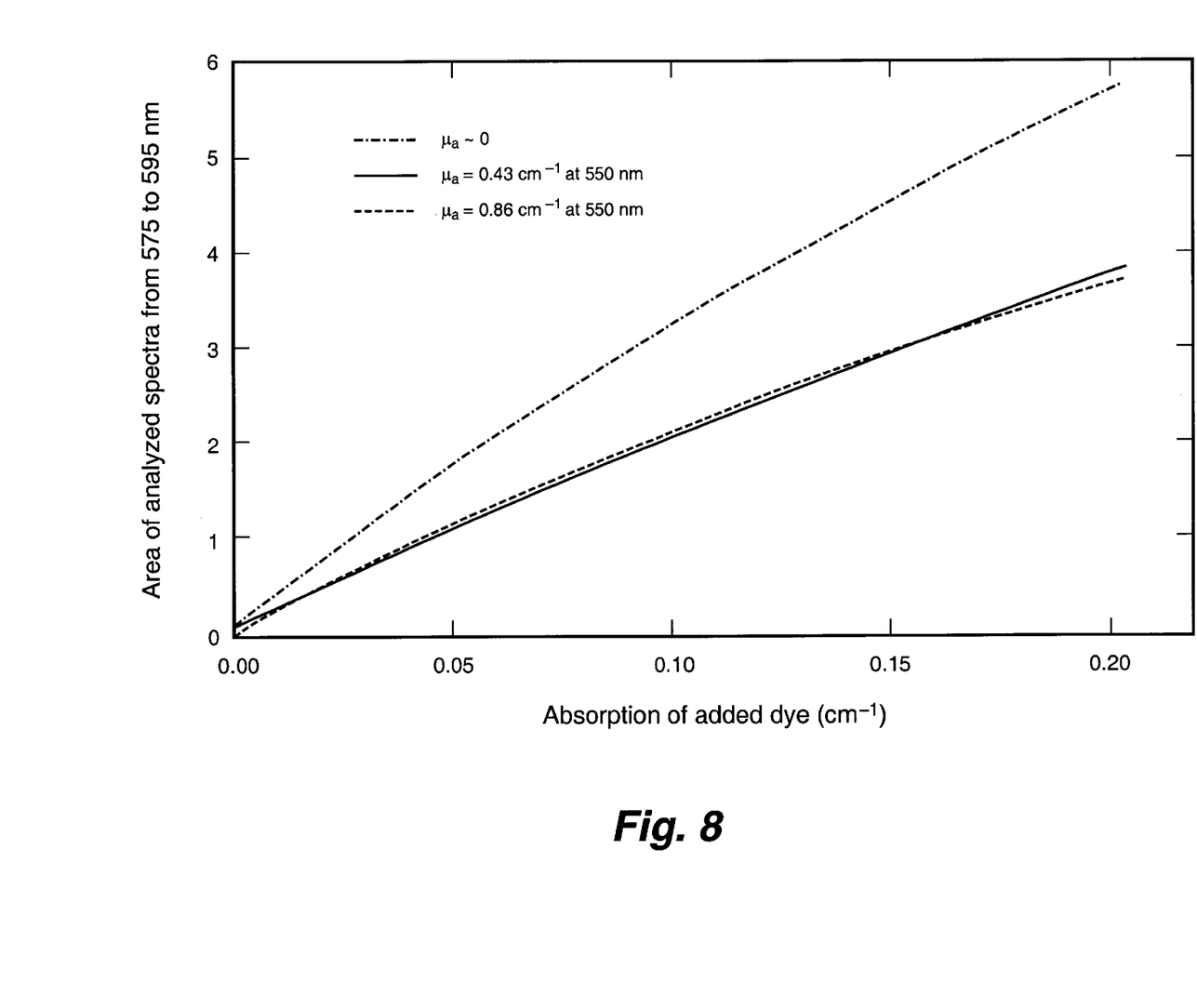
FIG. 8 shows the best values of the area of analyzed spectra from 575 to 595 nm as a function of the amount of added absorber for a fiber separation of 1.7 mm for three different values of background absorption. These curves were obtained by fitting raw data (similar to that shown in FIG. 4(a)) to a third-order polynomial.

The amount of Direct Blue dye added to a scattering solution is now estimated. Measurements were made before and after the addition of Direct Blue dye to solutions of spheres to which India ink had been added to yield an absorption coefficient of 0.4 cm$^{-1}$ at 585 nm. The area under the analyzed spectra from 575 to 595 nm for a source-detector separation of 1.7 mm was then computed as before and compared with a calibration curve to determine the change in absorption coefficient. The calibration curve was obtained by fitting of a third-order polynomial simultaneously to the results of earlier measurements taken at a fiber separation of 1.7 mm on three polystyrene sphere suspensions (0.2%, 0.4%, and 0.6% by weight) with a background absorption of 0.4 cm$^{-1}$. This curve is shown in FIG. 8. The results of the measurements of absorption coefficients are given in Table 1. Differences in the measured and the actual absorption coefficient change varied from 0 to 20%.

The Monte Carlo and experimental results both indicate that for a particular choice of fiber separation the average pathlength of the collected photons is quite insensitive to the scattering parameters. The Monte Carlo results show explicitly that the average pathlength is nearly independent of scattering properties. The experimental results, however, do not directly measure the average pathlength, (L). In a semi-infinite medium there are an infinite number of routes that can be taken from the source to the detector (although very few photons travel some of the routes). Let $I_i$ be the number of photons that start on route i, and let c be any constant. Then $$-\ln\left(\frac{I}{I_o}\right) = -\ln\left[\frac{\sum_{i=1}^{\infty} I_i \exp(-\mu_a L_i)}{I_o}\right] \neq c\mu_a(L), \sum_{i=1}^{\infty} I_i < I_o^- \quad (4)$$

The fact that pathlength is independent of scattering properties can only be inferred from the experimental data based on the fact that the change in signal due to the addition of an absorber does not depend on scattering properties.

Nonetheless, it is believed by the present inventors that, on the basis of the experimental and computational results, it is a good approximation to say that for the correct choice of fiber separation the average pathlength essentially does not depend on the scattering properties.

For a range of scattering parameters relevant to tissue, and for the optical geometry studied here, the optimal fiber separation was found experimentally to be approximately 1.7 mm for absorption coefficients of 0–0.86 cm$^{-1}$. This is in reasonable agreement with the Monte Carlo results, which showed that for absorption coefficients of 0.1, 0.5, and 2 cm$^{-1}$ a fiber separation of 1.75 was within the range of optimal fiber separations for each absorption coefficient. For clinical applications the ability to make measurements through an endoscope is advantageous. The source-detector separation of 1.7 mm is less than the diameter of typical endoscope working channels. Therefore endoscopic measurements can take advantage of the fact that at a separation of 1.7 mm the pathlength does not depend significantly on the scattering parameters.

One area of interest is the measurement of the change in absorption due to the administration of a photodynamic therapy drug. The absorption coefficient of Photofrin in tissue is expected to be roughly 0.01–0.1 cm$^{-1}$ at 630 nm. The present method is therefore applicable to the determination of photodynamic drug therapy concentrations in tissue. Other chromophores of potential interest are hemoglobin and cytochrome oxidase. The present method is also applicable to the measurement of changes in blood oxygenation. Oxyhemoglobin and deoxyhemoglobin have several absorption bands with different molar extinction coefficients. Depending on how much the concentration of hemoglobin changes, an appropriate absorption band can be used to measure the change in concentration. These examples do not represent a conclusive list of absorbing compounds of clinical interest. Others include bilirubin, NADH, and chemotherapy drugs.

To take advantage of the fact that the pathlength is insensitive to the scattering parameters and to use Eq. (2) to determine the absorption coefficient, it is necessary to know the pathlength or to have a calibration relating the measurement to an absorption coefficient. The curves in FIG. 8 can be used to determine the amount of absorber (Direct Blue Dye) added to a scattering solution that has a background absorption of either ~0, 0.4, or 0.8 cm$^{-1}$. This approach was tested for $\mu_a$, =0.4 cm$^{-1}$ and the results are presented in the TABLE. In all cases the errors in the measured change in absorption were less than 20%.

TABLE

| Solution Type (%0.913 μm spheres) | Measured Change in Absorbance (cm$^{-1}$) | Actual Change Absorbance (cm$^{-1}$) | in Error (%) |
| --- | --- | --- | --- |
| 0.2 | 0.027 | 0.033 | 18 |
| 0.2 | 0.070 | 0.076 | 7.9 |
| 0.4 | 0.018 | 0.022 | 18 |
| 0.4 | 0.077 | 0.065 | 18 |
| 0.6 | 0.128 | 0.108 | 19 |
| 0.6 | 0.152 | 0.129 | 18 |

Figure 9:
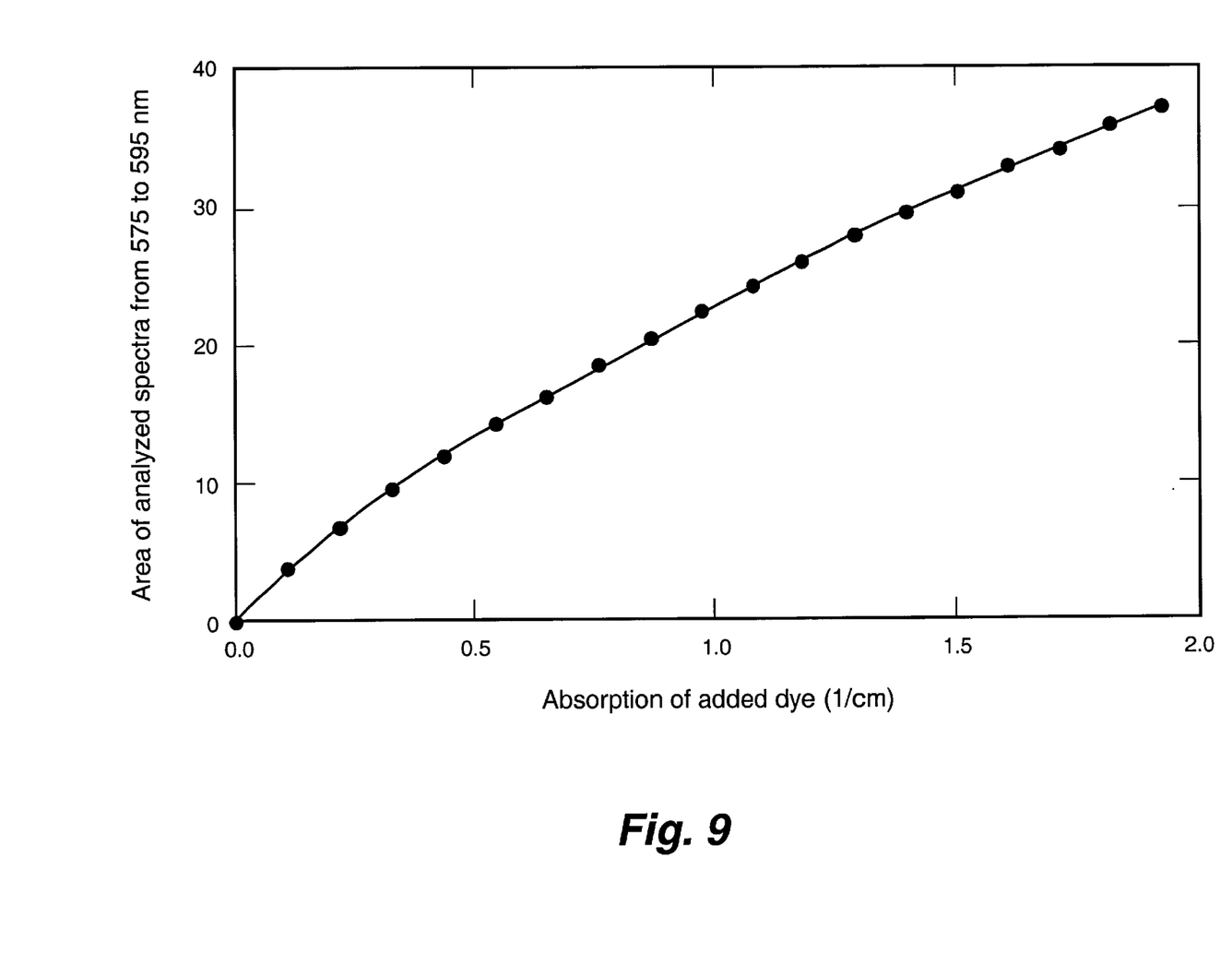
FIG. 9 shows areas under the curve from 575 to 595 nm of analyzed spectra plotted as a function of the average absorption coefficient of the blue dye from 575 to 595 nm; dye was added to the scattering solutions for a source-detector separation of 1.7 mm. The scattering media was 10% Intralipid-10% and background $\mu_a \approx 0$. The nonlinearity of the curve for small values of $\mu_a$ and the linearity of the curve at larger values of $\mu_a$ have, important consequences for how accurately the background absorbance must be known.

The curves for background absorption coefficients of $\mu_a$, 0 and $\mu_a$=0.4 cm$^{-1}$ in FIG. 8 are different from each other, although the curves for $\mu_a$=0.4 cm$^{-1}$ and $\mu_a$=0.8 cm$^{-1}$ are very similar. This can be understood by examining the results in FIG. 9, in which the area of analyzed spectra from 575 to 595 nm is plotted against the absorption coefficient of added Direct Blue dye (background $\mu_a$~0). The first part of this curve is steepest, consistent with the trace for $\mu_a$~0 having the steepest slope of the traces in FIG. 8. For values of $\mu_a$ greater than 0.4 cm$^{-1}$ the slope of the curve in FIG. 9 does not change very much, and this slope is smaller than the initial slope. Similarly, in FIG. 8 the slopes of the curves for background $\mu_a$=0.4 cm$^{-1}$ and $\mu_a$=0.8 cm$^{-1}$ are very similar, and both are less than that for $\mu_a$~0. (The slope of the curve for $\mu_a$>0.4 cm$^{-1}$ is what one would expect when adding blue dye starting from an average background absorption of 0.4 cm$^{-1}$ at 585 nm). The fact that the curves for background $\mu_a$~0 and $\mu_a$=0.4 cm$^{-1}$ are different means that, to take advantage of the fact that the average pathlength traveled by collected photons is insensitive to the scattering properties, it is necessary to know approximately the original background absorption. Based on the 20% variation (see FIG. 4(a)) in the areas from 575 to 595 nm of the analyzed spectra, the background absorption coefficient must be known to an accuracy of ~0.2 cm$^{-1}$ if it is between 0 and 0.4 cm$^{-1}$. For larger values of background $\mu_a$, one does not need to know $\mu_a$ as accurately, but only to an accuracy of ~2 cm$^{-1}$, as estimated from FIG. 9. In some cases it may be possible to estimate the background absorption based on a priori knowledge of the tissue being measured. Furthermore, if the background absorption varies by more than 0.2 cm$^{-1}$ across the wavelength range in which the species of interest absorbs, the approximation that the pathlength is independent of wavelength made in Section 2 becomes invalid.

Finally, it is noted that, although the actual measurements were performed in 50-ml beakers, the actual volume of the scatterer sampled by the light was much smaller. Monte Carlo simulations show that for a fiber separation of 1.48 mm the actual volume interrogated is ~0.1 cm$^3$ for g=0.9 and $\mu_s$=100 cm$^{-1}$.

In conclusion, by using both computational methods and experimental data, it is shown that for the correct choice of source-detector separation, the average photon pathlength is essentially independent of scattering properties. For the Monte Carlo simulations the tissue-relevant range of parameters investigated was 7.5<$\mu_s$<15 cm$^{-1}$ with g kept in the range 0.8<g<0.95. In the experimental measurements a larger range of parameters was investigated, with measurements made in suspensions with $\mu_s$' as large as 22 cm$^{-1}$. The optimum choice of center-to-center separation of the source and the detector fibers was found experimentally to be ~1.7 mm. This distance is smaller than the working channel of many endoscopes. Therefore, with a carefully designed probe, such as the probe illustrated in FIG. 2c hereof, it should be possible to take advantage of this effect in endoscopic optical measurements.

To test the utility of the average pathlengths being insensitive to scattering parameters, measurements were made of suspensions to which unknown amounts of absorber had been added, and the absolute concentrations of the added absorber were deduced. All the measured values were within 20% of the correct values. This demonstrates the utility of the present method, which does not require the use of a reflectance standard, for measuring small absorption changes. That the average pathlength is essentially independent of scattering properties is important for making measurements of small changes in absorption. Possible applications include concentration measurements of NADH, bilirubin, oxyhemoglobin, deoxyhemoglobin, photodynamic therapy drugs, and chemotherapy drugs.

The foregoing description of the invention has been presented for purposes of illustration and description and is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for measuring absorption of light by a material in small volume of highly scattering medium, which comprises in combination:

(a) a source of light having a wavelength which is absorbed by said material;

(b) a first optical fiber, having a first end for receiving the light from said source of light, and a second end for directing the light into the surface of the highly scattering medium, such that the light enters said highly scattering medium;

(c) a second optical fiber, having a first end located approximately 1.7 mm from the second end of said first optical fiber on the surface of said highly scattering medium, for collecting and receiving a portion of the light scattered from the highly scattering medium in a direction opposite to the light entering the highly scattering medium, and a second end, whereby the dependence of the pathlength of the light traversing the highly scattering medium taken to reach the first end of said second fiber on the scattering parameters of the highly scattering medium is minimized; and (d) a light detector for detecting light exiting the second end of said second optical fiber, such that a measurement of the light absorbed by a portion of the material is obtained.

2. The apparatus for measuring absorption of light by a material in a small volume of highly scattering medium, as described in claim 1, wherein the diameter of said first optical fiber and the diameter of said second optical fiber are less than 400 $\mu$m.

3. The apparatus for measuring absorption of light by a material in a small volume of highly scattering medium, as described in claim 1, further comprising a first mirror for receiving light emerging from the second end of said first optical fiber and for directing the light onto the surface of the highly scattering medium, such that the light enters said highly scattering medium, and a second mirror for collecting and receiving a portion of the light scattered from the highly scattering medium in a direction opposite to the light entering the highly scattering medium and for directing the received light onto the first end of said second optical fiber.

4. The apparatus for measuring absorption of light by a material in a small volume of highly scattering medium, as described in claim 1, wherein the second end of said first optical fiber and the first end of said second optical fiber are placed in direct optical contact with the surface of the highly scattering medium in order to reduce reflections from the surface from entering the first end of said second optical fiber.

5. The apparatus for measuring absorption of light by a material in a small volume of highly scattering medium, as described in claim 1, wherein said source of light is a monochromatic source of light.

6. The apparatus for measuring absorption of light by a material in a small volume of highly scattering medium, as described in claim 1, wherein said source of light is a polychromatic source of light and said apparatus further comprises a spectrograph for receiving the light exiting the second end of said second optical fiber and selecting a chosen wavelength therefrom, such that the chosen wavelength is detected by said light detector.

7. The apparatus for measuring absorption of light by a material in a small volume of highly scattering medium, as described in claim 6, wherein said polychromatic source of light is selected from the group consisting of xenon and tungsten arc lamps.

8. The apparatus for measuring absorption of light by a material in a small volume of highly scattering medium, as described in claim 1, wherein means are provided for measuring the intensity of said source of light.

* * * * *